United States Patent [19]

Passafaro

[11] Patent Number: 4,651,741
[45] Date of Patent: Mar. 24, 1987

[54] METHOD AND APPARATUS FOR DETERMINING OXYGEN SATURATION IN VIVO

[75] Inventor: James D. Passafaro, Santa Ana, Calif.

[73] Assignee: Baxter Travenol Laboratories, Inc., Deerfield, Ill.

[21] Appl. No.: 739,546

[22] Filed: May 30, 1985

[51] Int. Cl.$^4$ ............................................. A61B 5/00
[52] U.S. Cl. .................................. 128/633; 128/637; 356/41
[58] Field of Search ............... 128/633, 634, 632, 637; 356/39, 40, 41, 309

[56] References Cited

U.S. PATENT DOCUMENTS

| | | | |
|---|---|---|---|
| 3,825,342 | 7/1974 | Lubbers et al. | 356/41 |
| 3,847,483 | 11/1974 | Shaw et al. | 356/41 |
| 4,114,604 | 9/1978 | Shaw et al. | 128/634 |
| 4,266,554 | 5/1981 | Hamaguri | 356/41 X |

OTHER PUBLICATIONS

"Effects of Multiple Scattering and Peripheral Circulation on Arterial Oxygen Saturation Measured with a Pulse-Type Oximeter", Medical & Biological Engineering & Computing, Y. Shimada et al, pp. 475–479, Sep. 1984.

Primary Examiner—Stephen F. Husar
Attorney, Agent, or Firm—Weissenberger and Peterson

[57] ABSTRACT

Accurate in vivo measurement of blood oxygen saturation by fiberoptical means is made possible throughout a wide range of hematocrit or total hemoglobin values by using a single R/IR ratio I and calculating the $SO_2$ value therefrom through the use of a second-order polynomial of the form $$SO_2 = Ak^2I^2 + BkI + C$$

in which A, B and C are hematocrit or total hemoglobin-dependent coefficients. These values may be contained in a lookup table accessed by a hematocrit or total hemoglobin value selection, and k is a purely multiplicative calibration constant which can be readily determined for any individual fiberoptic system.

9 Claims, 6 Drawing Figures

METHOD AND APPARATUS FOR DETERMINING OXYGEN SATURATION IN VIVO

FIELD OF THE INVENTION

This invention relates to the optical measurement of oxygen saturation in blood, and more particularly to a method and apparatus for providing a simpler and more accurate measurement than was previously possible.

BACKGROUND OF THE INVENTION

Blook oxygen saturation ($SO_2$) is conventionally measured in vivo by inserting a fiber optic catheter into a blood vessel and detecting the relative reflectivity of the blood under red and infrared illumination. In one prior art device, an intensity ratio $I = \lambda_2/\lambda_1$ was determined from a red intensity signal $\lambda_1$ and in infrared intensity signal $\lambda_2$. A linear transfer function of the form $SO_2 = BI + A$ was used to provide the saturation indication, with A being determined at the time of manufacture and B being obtained by adjustment of a calibration knob after intubation to match an in vitro analysis of a blood sample taken from the patient. This method provided accurate information only at the saturation level at which the sample was taken, and approximate information at all other levels.

Another prior art method (see U.S. Pat. No. 4,114,604) used three intensity signals $\lambda_1$, $\lambda_2$, and $\lambda_3$ (typically on the order of 670, 700 and 800 nm respectively) from which two ratios $I_1 = \lambda_1/\lambda_2$ and $I_3/\lambda_2$ were determined. The transfer function for the saturation indication was of the general form.

$$SO_2 = \frac{A_0 + A_1 I_1 + A_2 I_3}{B_0 + B_1 I_1 + B_2 I_3}$$

or $$SO_2 = \frac{A_0 + A_1 I_1 + A_2 I_1^2 + A_3 I_3}{B_0 + B_1 I_1 + B_2 I_1^2 + B_3 I_3}$$

in which the A and B factors were selectively weighted so as to minimize the effect of varying physiological characteristics of the blood under test. Calibration in this method involved both additive and multiplicative aspects of the optical measurements. Nevertheless, the transfer function of this method produced still only an approximation of the real $SO_2$ values, particularly at hematocrits differing substantially from a nominal hematocrit of about 35%.

SUMMARY OF THE INVENTION

The present invention uses only a single intensity ratio $I = \lambda_1/\lambda_2$ where $\lambda_1 \approx 660$ nm and $\lambda_2 \approx 810$ nm. The transfer function, however, is a second order polynomial of the general form $$SO_2 = AI^2 + BI + C$$

in which A, B and C are hematocrit or total hemoglobin-dependent coefficients whose absolute values are different for different fiberoptic systems, but whose relation to one another remains constant for all systems. Consequently, the calibration of the inventive apparatus is a multiplicative operation only.

It is thus the object of the invention to provide a method and apparatus for accurately measuring blood oxygen saturation, in which the apparatus can be calibrated by a purely multiplicative operation.

It is another object of the invention to achieve this result by using a transfer function having the form of a second order polynomial whose constants have a uniform proportionality to each other for all fiberoptic systems.

DESCRIPTION OF THE PREFERRED EMBODIMENT

Blood oxygen saturation is typically measured by inserting a fiberoptic device into a blood conduit and positioning its tip at a point in the blood conduit where proper oxygen saturation is most critical. Light is transmitted to the distal tip through one fiber of the device, and the light reflected by the blood stream is returned to the outside of the body through the other fiber. The intensity of the reflected light at predetermined wavelengths in the red and infrared portions of the spectrum (preferably 660 nm and 810 nm) is sensed by appropriate optoelectronic devices to provide the input signals to the oxygen saturation measuring instrument.

Prior to intubation the fiberoptic system may be calibrated in vitro by measuring its response to a target of standard color and reflectivity.

Subsequently, the instrument may be calibrated in vivo by drawing a blood sample for laboratory analysis and relating a standard ratio derived from the laboratory oximeter value with the intensity ratio recorded at the time the blood sample was drawn.

Figure 1:
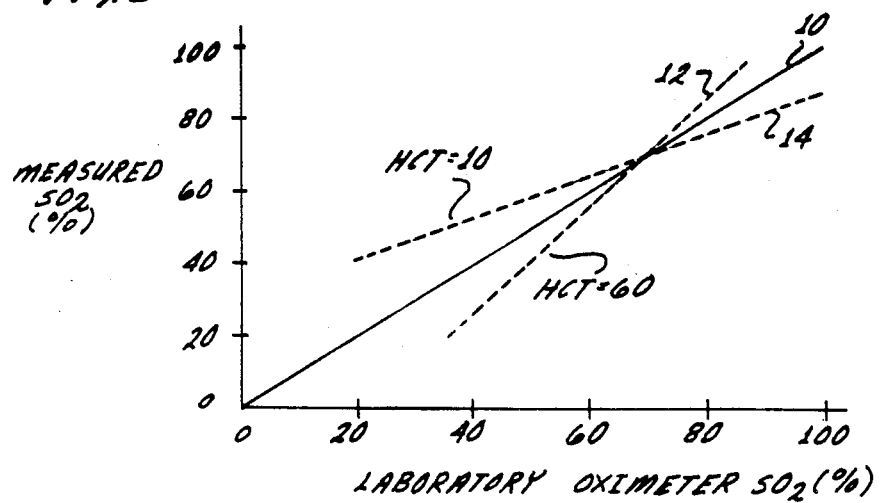
FIG. 1 is a tracking graph illustrating the effect of hematocrit (or total hemoglobin, which is generally directly proportional thereto) changes on the correspondence between calculated $SO_2$ values and laboratory-determined $SO_2$ values.

If the instrument is properly calibrated and uses an accurate transfer function, the reading calculated from the red/infrared intensity ratio should match the laboratory oximeter at all saturation levels (line 10 in FIG. 1). However, this is not normally the case for two reasons. First, conventional instruments are sensitive to the hematocrit (HCT) of the blood and tend to track increasingly poorly as the hematocrit or total hemoglobin deviates from the generally accepted calibration level of 35% or 11.2 g/dl, respectively (lines 12, 14 of FIG. 1).

Unfortunately, sick patients tend to have hematocrits outside the normal range. In the vicinity of the calibration blood oxygen saturation level, in this example 70%, hematocrit changes have little effect, as shown by FIG. 1, but at materially different saturation levels, a significant error can occur with conventional instruments in a very sick patient.

The second tracking problem arises from the fact that the ratio/saturation curve not only changes with the hematocrit, but is also nonlinear. Prior art instruments have either ignored the nonlinearity or have attempted to compensate for it in various ways by using complex transfer functions requiring, in some instances, more than two spectral intensity signals. In addition, the complexity of the prior art transfer function required the use of both multiplicative and additive operations to achieve calibration of individual fiberoptic systems.

Figure 3:
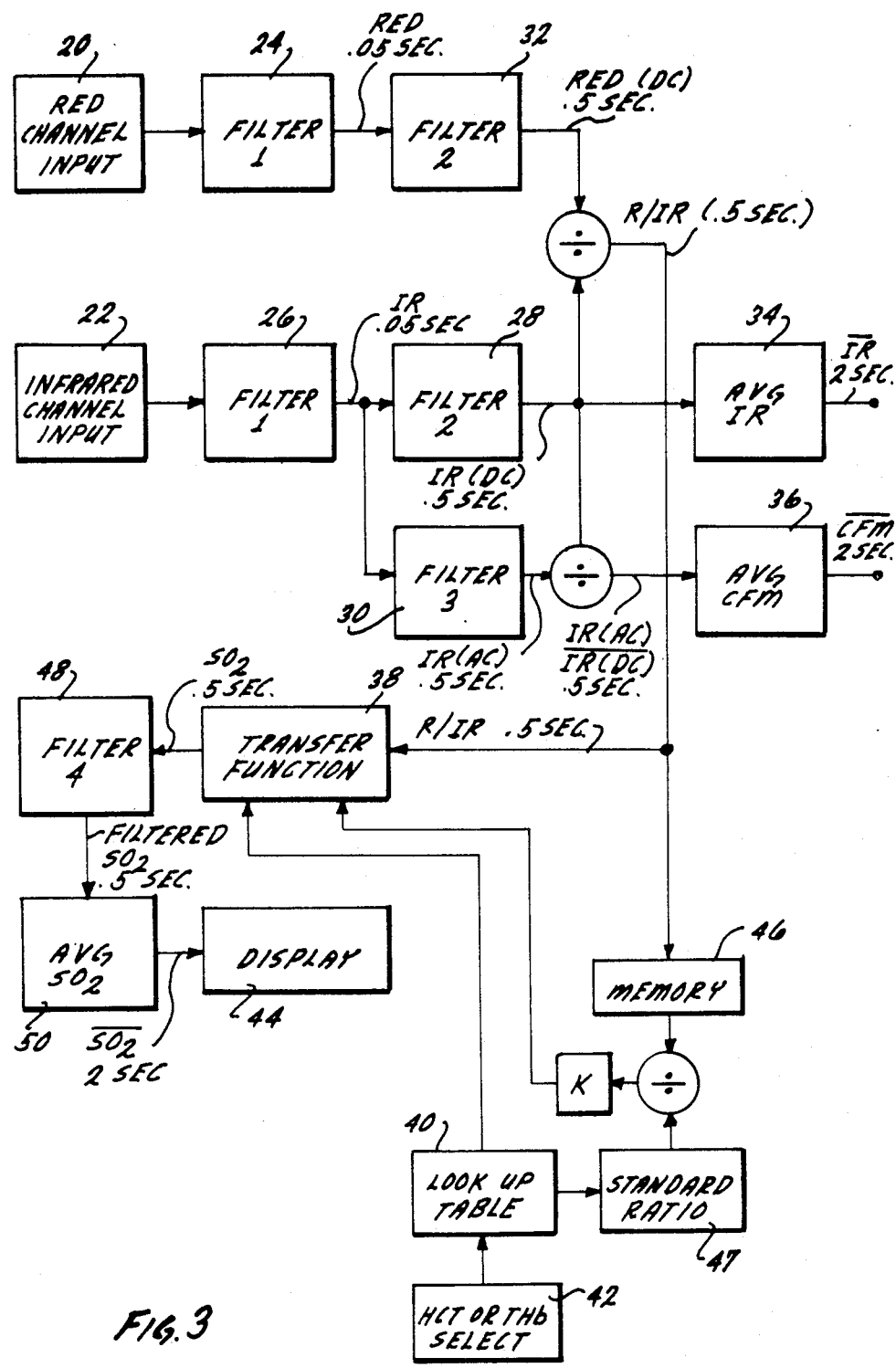
FIG. 3 is a block diagram illustrating the signal processing in the inventive apparatus.

The general operation of the apparatus of this invention is shown in FIG. 3. The red intensity signal is applied to input terminal 20, and the infrared intensity signal is applied to input terminal 22. Both signals are averaged over 50 ms intervals by filters 24, 26, respectively. The DC and AC components of the IR signal, and the DC component of the R signal, are then filtered individually by filters 23, 30, 32, respectively, to produce IR(DC), IR(AC), and R(DC) outputs averaged over half-second intervals. The purpose of the foregoing filtration is noise reduction by eliminating the effects of heartbeat and respiration.

The IR(DC) signal is averaged over 2-second intervals by filter 34 to produce a means-IR output for purposes described in the copending application Ser. No. 656,515 filed Oct. 1, 1984, and entitled CARDIAC FLOW MONITOR. The IR(AC) signal is divided by the IR(DC) signal and then averaged over 2-second intervals by filter 36 to produce a cardiac flow monitor signal, again as described in the aforesaid copending application.

The filtered R(DC) signal is next divided by the filtered IR(DC) signal to produce the intensity ratio I=R(DC)/IR(DC). The oxygen saturation level is calculated from this ratio, according to the present invention, through the use of a simple quadratic transfer function 38

$$SO_2 = Ak^2I^2 = BkI + C$$

in which A, B, and C are hematocrit-dependent constants which may be contained in a look-up table 40 accessed by a laboratory-determined hematocrit selection 42.

In the transfer function 38, k is a calibration constant which is determined for each individual fiber-optic system by in vitro or in vivo calibration as described above. In the latter case, the intensity ratio measured at the time of taking a blood sample from the patient is stored in a memory 46. After the sample has been analyzed by the laboratory, the value in memory 46 can be divided by a standard ratio computed on the basis of the sample's hematocrit and the look-up table 40 in a ratio former 47 so as to correspond to the laboratory-determined oximeter values in order to produce the calibration constant k. Alternatively, for in vitro calibration, k can be calculated by dividing the intensity ratio reflected by the calibration target and stored in memory 46 by the standard value of the calibration target.

The $SO_2$ value calculated by using the transfer function 38 is next filtered by a damping filter 48 to prevent display flicker. The damped $SO_2$ signal is then averaged over 2-second intervals by filter 50 to produce a mean $SO_2$ value which can be displayed in display 44.

The hematocrit selection in the present invention is not automatic. However, hematocrit levels tend to change very slowly and (in a surgical environment) predictably. Consequently, the physician, knowing the effect the surgical procedure will have on the patient's hematocrit level, can either choose an average hematocrit setting or arrange for the hematocrit setting to be modified as the surgical procedure progresses.

Figure 4:
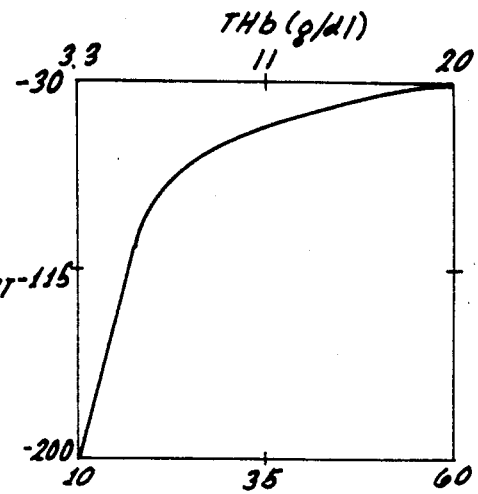
FIG. 4 is a coefficient-hematocrit diagram showing the values of A for various hematocrits.
Figure 5:
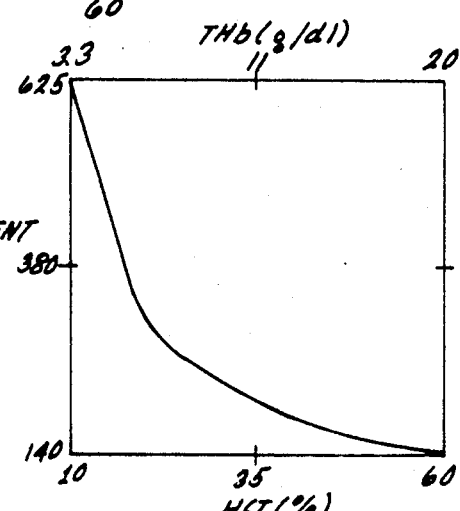
FIG. 5 is a coefficient-hematocrit diagram showing the values of B for various hematocrits.
Figure 6:
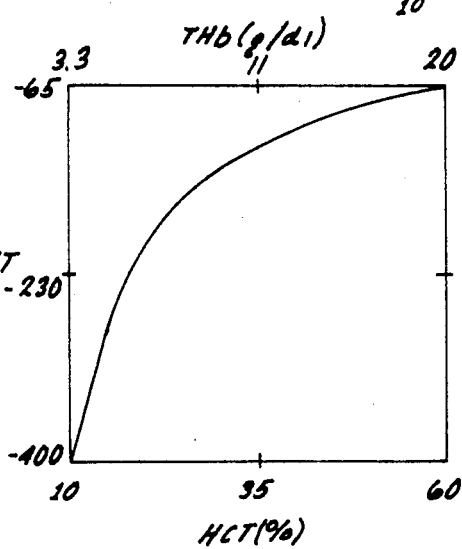
FIG. 6 is a coefficient-hematocrit diagram showing the values of C for various hematocrits.

FIGS. 4, 5 and 6 show the values of the coefficients A, B and C in accordance with this invention as a function of the hematocrit level. A look-up table such as 40 (FIG. 3) is a convenient tool for obtaining the greatest accuracy where it is most needed, for example by providing separate sets of coefficients at 1% intervals for the critical hematocrit levels lying between 10% and 30%, and at greater intervals in the less critical hematocrit ranges.

Figure 2:
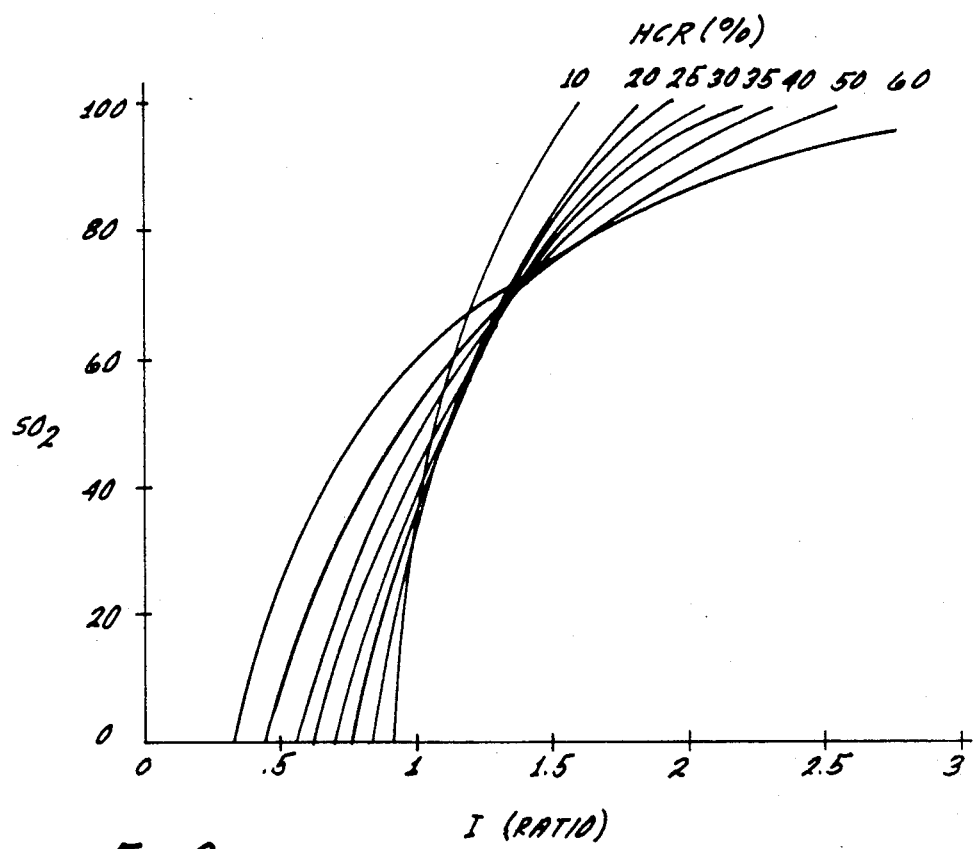
FIG. 2 is a ratio-saturation diagram showing the relation of blood oxygen saturation to the ratio $\lambda_1/\lambda_2$ for various values of hematocrit.

As will be seen from FIG. 2, the ratio-saturation curve for any given level of hematocrit is very closely parabolic in shape. Consequently, it is accurately expressible as a simple quadratic equation, and the ability of the present invention to adjust the coefficients of the equation for individual hematocrit levels dispenses with the need for complex transfer functions.

In the preferred embodiment of the invention, the calculations leading to the determination of the $SO_2$ value are performed by a microprocessor to which digitized R and IR signals are applied, and which can be appropriately programmed in accordance with conventional programming techniques. However, it should be understood that the invention is not so limited, and that the calculation of $SO_2$ could also be carried out from analog input signals by conventional analog computing circuitry.

What is claimed is:

1. The method of measuring blood oxygen saturation in vivo comprising:
    obtaining a pair of signals indicative of the reflectivity of the blood being measured in the red and infrared portions of the light spectrum, respectively;
    forming the ratio I of said signals;
    establishing the hematocrit level of said blood; and
    determining the oxygen saturation $SO_2$ of said blood by the equation $$SO_2 = Ak^2I^2 + BkI + C$$

in which A, B, and C are Hematocrit-dependent coefficients and k is a calibration constant.

2. The method of claim 1 in which k is calculated by storing the value of said ratio at the time of taking a blood sample, ascertaining the actual saturation values of said sample in vitro, determining a standard value of said ratio corresponding to said actual saturation and hematocrit values, and making k equal to the ratio of said determined value to said stored value.

3. Apparatus for measuring blood oxygen saturation in vivo, comprising:
    optical means for illuminating blood within a blood conduit and providing a reflection therefrom;
    sensing means for providing signals representative of the intensity of said reflection at a pair of wavelengths in the red and infrared portion of the spectrum, respectively;
    divider means for forming the ratio I of said red to said infrared signals;
    hematocrit selection means for selecting a hematocrit value corresponding to the hematocrit of said blood;
    saturation determining means for determining an oxygen saturation value $SO_2$ from said ratio in accordance with the transfer function $$SO^2 = Ak^2I^2 + BkI + C$$

in which A, B, and C are hematocrit-dependent coefficients and in which k is a calibration constant; and display means for displaying said determined $SO_2$ value.

4. The apparatus of claim 3 further comprising:

memory means for storing the value of said ratio at the time of taking a blood sample;

entry means for entering the actual $SO_2$ and hematocrit values of said sample;

computing means for computing an intensity ratio corresponding to said $SO_2$ value; and quotient-forming means for forming the quotient of said computed ratio value to said stored value, said quotient being k.

5. The apparatus of claim 3 further comprising calibration means for calculating k so as to provide an $SO_2$ display consistent with the known $SO_2$ value of a standard reflector during in vitro calibration.

6. The apparatus of claim 3 further comprising look-up table means for storing the values of A, B and C for a plurality of hematocrit levels, said look-up table means being controlled by the selection of a hematocrit level at which blood oxygen saturation is to be measured.

7. The apparatus of claim 3, wherein A, B and C have uniform proportionality to each other for different systems.

8. The apparatus of claim 3 wherein the absolute values of A, B and C decrease with increasing hematocrit.

9. The apparatus of claim 8 wherein the absolute value of B decreases more than the absolute values of A and C between 10% and 60% hematocrit.

* * * * *